(12) United States Patent
Calhoun

(10) Patent No.: US 9,956,001 B2
(45) Date of Patent: May 1, 2018

(54) DERMAL ABRASION SYSTEM

(71) Applicant: Dominique Calhoun, Lemon Grove, CA (US)

(72) Inventor: Dominique Calhoun, Lemon Grove, CA (US)

(*) Notice: Subject to any disclaimer, the term of this patent is extended or adjusted under 35 U.S.C. 154(b) by 310 days.

(21) Appl. No.: 14/981,249

(22) Filed: Dec. 28, 2015

(65) Prior Publication Data
US 2017/0181769 A1 Jun. 29, 2017

(51) Int. Cl.
*A61B 17/50* (2006.01)
*A61B 17/54* (2006.01)
*A61K 9/06* (2006.01)
*A61K 9/00* (2006.01)

(52) U.S. Cl.
CPC ............ *A61B 17/54* (2013.01); *A61K 9/0014* (2013.01); *A61K 9/06* (2013.01)

(58) Field of Classification Search
CPC ....... A61B 17/54; A61B 17/545; A61B 17/50; A61B 2017/505; A61B 2017/00747; A61B 2017/00752; A61B 2017/00761; A61K 9/0014; A61K 9/06
See application file for complete search history.

(56) References Cited

U.S. PATENT DOCUMENTS

| | | | |
|---|---|---|---|
| 2,507,619 A | 5/1950 | Anderson | |
| 2,886,840 A | 5/1959 | Spratlin | |
| 6,162,232 A * | 12/2000 | Shadduck | A61B 17/545 604/289 |
| 6,299,620 B1 * | 10/2001 | Shadduck | A61B 17/54 604/289 |
| 6,911,031 B2 * | 6/2005 | Muldner | A61B 17/54 606/131 |
| D563,613 S | 3/2008 | Barringer | |
| 7,572,238 B2 * | 8/2009 | Rhoades | A45D 34/041 601/138 |
| 2002/0193061 A1 * | 12/2002 | Park | A61B 17/54 451/557 |
| 2003/0187462 A1 * | 10/2003 | Chang | A61B 17/54 606/131 |
| 2004/0016438 A1 * | 1/2004 | Han | A45D 29/18 132/75.4 |
| 2004/0092895 A1 * | 5/2004 | Harmon | A61B 17/54 604/289 |
| 2004/0122447 A1 * | 6/2004 | Harmon | A61B 17/54 606/131 |
| 2005/0278877 A1 | 12/2005 | Akridge | |
| 2006/0010625 A1 | 1/2006 | Tapper et al. | |
| 2006/0052805 A1 | 3/2006 | Cwik | |
| 2010/0222719 A1 | 9/2010 | Cowle et al. | |

(Continued)

FOREIGN PATENT DOCUMENTS

WO WO0113775 3/2001

*Primary Examiner* — Jonathan Miles

(57) ABSTRACT

A dermal abrasion system includes a cream that may be applied to skin thereby facilitating the cream to liquefy contaminants in the skin. A scraper is provided and the scraper may be manipulated. The scraper frictionally engages the cream when the cream is applied to the skin. The scraper abrades the liquefied contaminants from the skin thereby enhancing cleanliness of the skin. The scraper has a scraping edge. The scraping edge is continuous such that the scraper may abrade the skin from a selected angle.

5 Claims, 3 Drawing Sheets

(56) References Cited

U.S. PATENT DOCUMENTS

| | | | | |
|---|---|---|---|---|
| 2013/0138119 A1* | 5/2013 | Luzon | .................... | A61B 17/54 |
| | | | | 606/131 |
| 2014/0378887 A1* | 12/2014 | Chang | ................... | A61M 37/00 |
| | | | | 604/20 |
| 2015/0051620 A1* | 2/2015 | Presser | ................. | A61B 17/54 |
| | | | | 606/131 |
| 2015/0182256 A1* | 7/2015 | Berk | ...................... | A61B 17/50 |
| | | | | 606/127 |
| 2015/0182291 A1* | 7/2015 | Grez | ..................... | A61B 19/40 |
| | | | | 601/2 |

\* cited by examiner

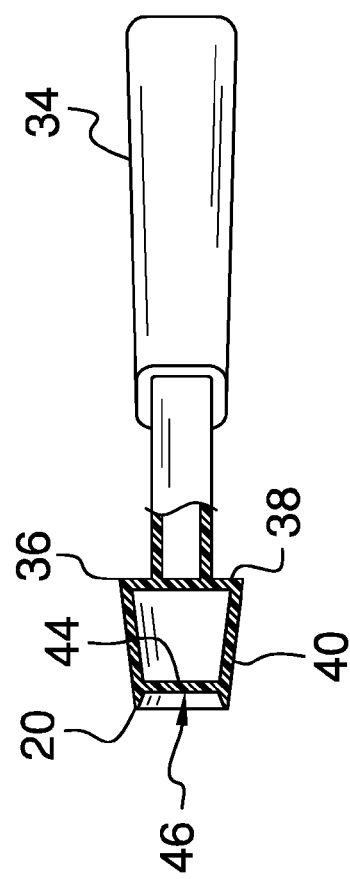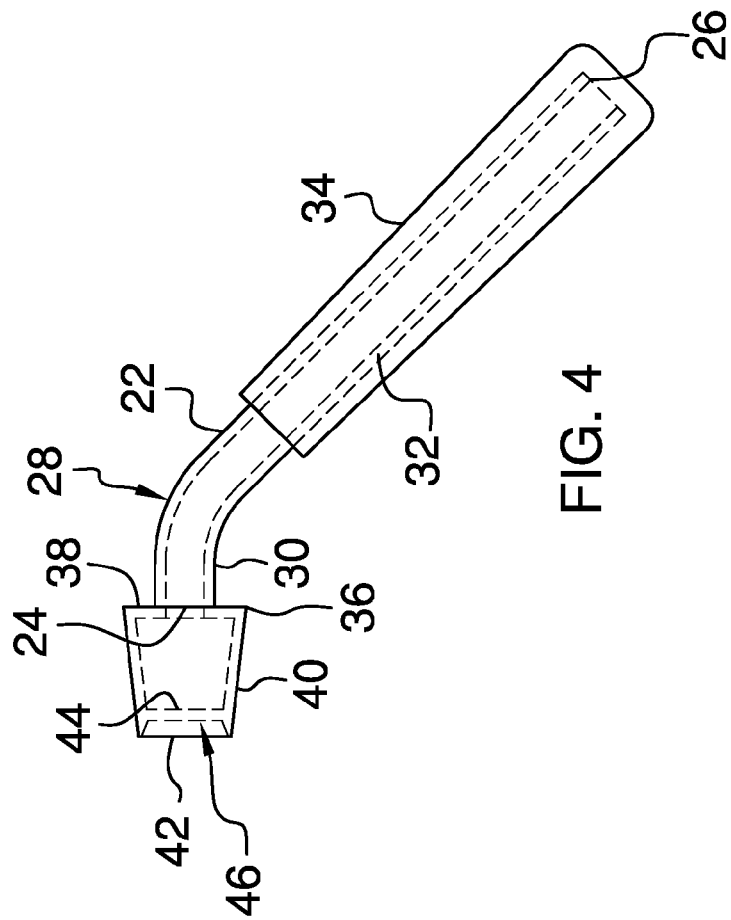

DERMAL ABRASION SYSTEM

BACKGROUND OF THE DISCLOSURE

Field of the Disclosure

The disclosure relates to abrasion devices and more particularly pertains to a new abrasion device for abrading skin in combination with a cream to remove dead skin cells while also cleansing the skin.

SUMMARY OF THE DISCLOSURE

An embodiment of the disclosure meets the needs presented above by generally comprising a cream that may be applied to skin thereby facilitating the cream to liquefy contaminants in the skin. A scraper is provided and the scraper may be manipulated. The scraper frictionally engages the cream when the cream is applied to the skin. The scraper abrades the liquefied contaminants from the skin thereby enhancing cleanliness of the skin. The scraper has a scraping edge. The scraping edge is continuous such that the scraper may abrade the skin from a selected angle.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein:

FIG. 3 is a top cut-away view of an embodiment of the disclosure.

FIG. 4 is a left side phantom view of an embodiment of the disclosure.

DESCRIPTION OF THE PREFERRED EMBODIMENT

Figure 2:
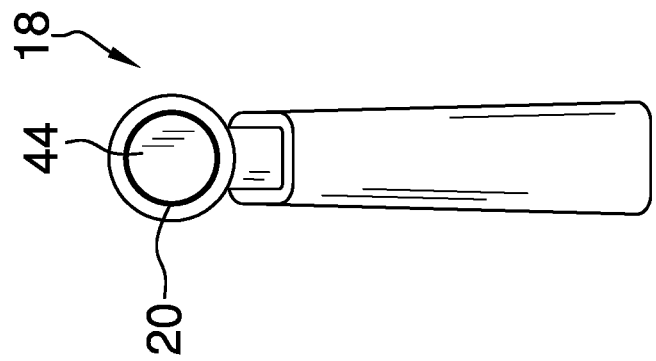
FIG. 2 is a front view of an embodiment of the disclosure.
Figure 1:
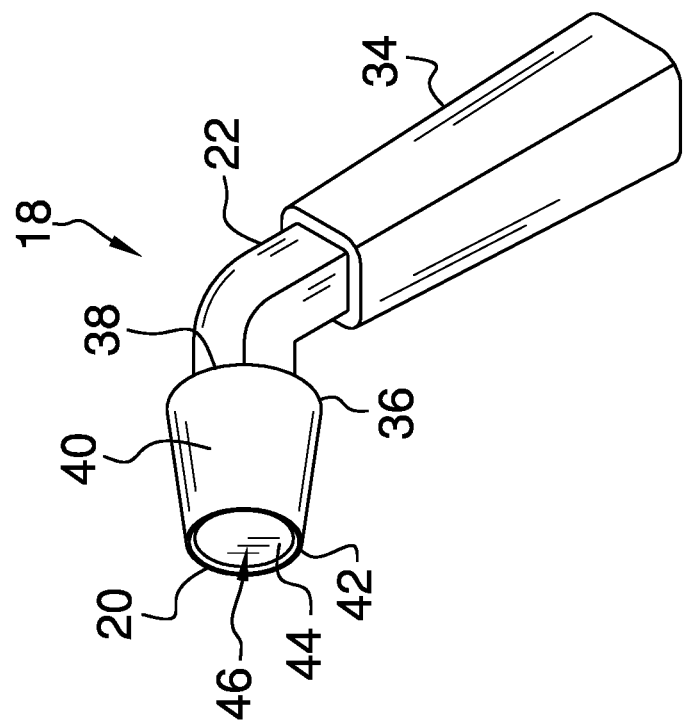
FIG. 1 is a perspective view of a dermal abrasion system according to an embodiment of the disclosure.
Figure 5:
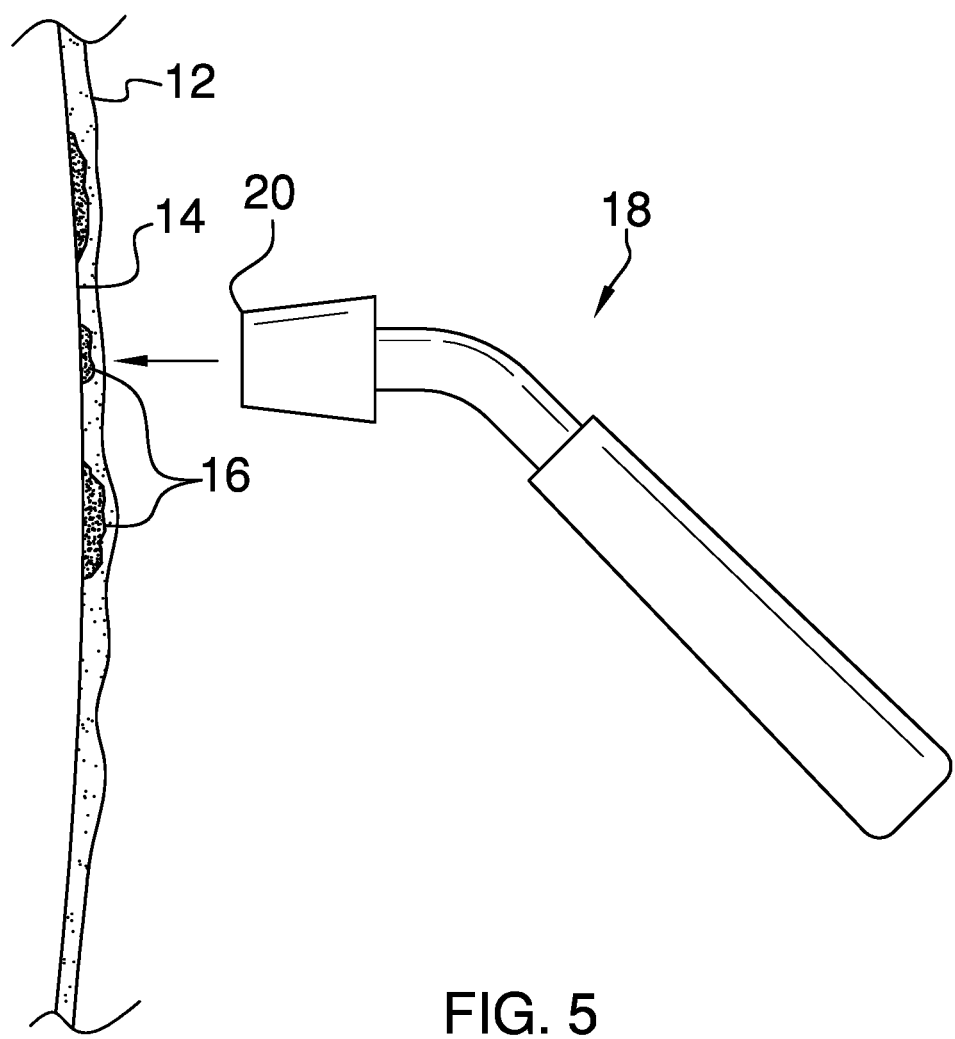
FIG. 5 is a perspective in-use view of an embodiment of the disclosure.

With reference now to the drawings, and in particular to FIGS. 1 through 5 thereof, a new abrasion device embodying the principles and concepts of an embodiment of the disclosure and generally designated by the reference numeral 10 will be described.

As best illustrated in FIGS. 1 through 5, the dermal abrasion system 10 generally comprises a cream 12 that may be applied to skin 14 thereby facilitating the cream 12 to liquefy contaminants 16 in the skin 14. The cream 12 may comprise a facial mask, a facial soap or other facial hygiene cream. The skin 14 may be skin on a person's face. The liquefied contaminants 16 may comprise dirt, accumulated bacteria, dead skin cells and other contaminants associated with dirty skin.

A scraper 18 is provided and the scraper 18 may be manipulated. The scraper 18 frictionally engages the cream 12 when the cream 12 is applied to the skin 14. The scraper 18 is manipulated to abrade the liquefied contaminants 16 from the skin 14 thereby enhancing cleanliness of the skin 14. The scraper 18 has a scraping edge 20 and the scraping edge 20 is continuous. Thus, the scraper 18 may abrade the skin 14 from a selected angle.

The scraper 18 comprises a handle 22 that has a first end 24 and a second end 26. The handle 22 is elongated and the handle 22 has a bend 28 thereon to define a first section 30 and a second section 32. The bend 28 is positioned closer to the first end 24 than the second end 26. Thus, the first section 30 has a length that is greater than a length of the second section 32. The second section 32 may be gripped.

A sleeve 34 is positioned around the handle 22. The sleeve 34 may be comprised of a resiliently compressible material. Thus, the sleeve 34 enhances gripping the handle 22. The sleeve 34 substantially covers the second section 32.

A cup 36 is provided that has a basal wall 38 and a peripheral wall 40 extending away from the basal wall 38. The peripheral wall 40 is continuous such that the cup 36 has a cylindrical shape. The peripheral wall 40 has a distal edge 42 with respect to the basal wall 38. The peripheral wall 40 tapers inwardly between the basal wall 38 and the distal edge 42. The distal edge 42 is sharpened to define the scraping edge 20.

The basal wall 38 is coupled to the first end 24 of the handle 22. Thus, the scraping edge 20 may frictionally engage the skin 14 when the handle 22 is manipulated. The handle 22 may be positioned at a selected angle with respect to the skin 14. The continuous nature of the scraping edge 20 ensures the scraping edge 20 may abrade the skin 14 regardless of the selected angle of the handle 22 with respect to the skin 14.

The cup 36 has a medial wall 44 positioned between the basal wall 38 and the distal edge 42. The medial wall 44 defines a reservoir 46 between the medial wall 44 and the distal edge 42. The reservoir 46 collects the liquefied contaminants 16 when the scraping edge 20 abrades the skin 14. The medial wall 44 is positioned closer to the distal edge 42 than the basal wall 38.

In use, the cream 12 is applied to the skin 14 and the cream 12 is allowed to dry. The handle 22 is gripped and the scraping edge 20 is positioned to frictionally engage the skin 14. The handle 22 is manipulated to urge the scraping edge 20 along the skin 14. The scraping edge 20 frictionally engages the skin 14 and the scraping edge 20 removes the liquefied contaminants 16 from the skin 14.

The liquefied contaminants 16 collect in the reservoir 46 as the scraping edge 20 is urged along the skin 14. The reservoir 46 is emptied when the reservoir 46 is filled with the liquefied contaminants 16. The cream 12 is entirely abraded from the skin 14 with the scraper 18. Thus, the scraper 18 removes the liquefied contaminants 16 from the skin 14 thereby enhancing health and cleanliness of the skin 14. The scraper 18 reduces symptoms of acne and other skin ailments. The scraper 18 may be used with or without the cream 12.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A dermal abrasion system comprising:
a cream being configured to be applied to skin thereby facilitating said cream to liquefy contaminants in the skin; and
a scraper being configured to be manipulated, said scraper frictionally engaging said cream when said cream is applied to the skin, said scraper being configured to abrade the liquefied contaminants from the skin thereby enhancing cleanliness of the skin, said scraper having a scraping edge, said scraping edge being continuous such that said scraper is configured to abrade the skin from a selected angle; a cup having a basal; wall and a peripheral wall extending away from said basal wall, said peripheral wall being continuous such that said cup has a cylindrical shape, said peripheral wall having a distal edge with respect to said basal wall, said peripheral wall tapering inwardly between said basal wall and said distal edge, said distal edge being sharpened to define said scraping edge;
wherein said cup has a medial wall being positioned between said basal wall and said distal edge, said medial wall being continuous and extending from said peripheral wall to form a solid barrier defining a reservoir between said medial wall and said distal edge, wherein said reservoir is configured to receive the liquefied contaminants when said scraping edge abrades the skin, said medial wall being positioned closer to said distal edge than said basal wall.

2. The assembly according to claim 1, wherein said scraper comprises a handle having a first end and a second end, said handle being elongated, said handle having a bend thereon to define a first section and a second section, said bend being positioned closer to said first end than said second end such that first section has a length being less than a length of said second section, said second section being configured to be gripped.

3. The assembly according to claim 2, further comprising a sleeve being positioned around said handle wherein said sleeve is configured to be gripped, said sleeve substantially covering said second section.

4. The assembly according to claim 1, wherein:
said scraper includes a handle, said handle having a first end; and
said basal wall being coupled to said first end of said handle wherein said scraping edge is configured to frictionally engage the skin when said handle is manipulated.

5. A dermal abrasion system comprising:
a cream being configured to be applied to skin thereby facilitating said cream to liquefy contaminants in the skin; and
a scraper being configured to be manipulated, said scraper frictionally engaging said cream when said cream is applied to the skin, said scraper being configured to abrade the liquefied contaminants from the skin thereby enhancing cleanliness of the skin, said scraper having a scraping edge, said scraping edge being continuous such that said scraper is configured to abrade the skin from a selected angle, said scraper comprising:
a handle having a first end and a second end, said handle being elongated, said handle having a bend thereon to define a first section and a second section, said bend being positioned closer to said first end than said second end such that first section has a length being less than a length of said second section, said second section being configured to be gripped,
a sleeve being positioned around said handle wherein said sleeve is configured to be gripped, said sleeve substantially covering said second section, and
a cup having a basal wall and a peripheral wall extending away from said basal wall, said peripheral wall being continuous such that said cup has a cylindrical shape, said peripheral wall having a distal edge with respect to said basal wall, said peripheral wall tapering inwardly between said basal wall and said distal edge, said distal edge being sharpened to define said scraping edge, said basal wall being coupled to said first end of said handle wherein said scraping edge is configured to frictionally engage the skin when said handle is manipulated, said cup having a medial wall being positioned between said basal wall and said distal edge, said medial wall being continuous and extending from said peripheral wall to form a solid barrier defining a reservoir between said medial wall and said distal edge wherein said reservoir is configured to receive the liquefied contaminants when said scraping edge abrades the skin, said medial wall being positioned closer to said distal edge than said basal wall.

* * * * *